United States Patent [19]

Kaneko et al.

[11] Patent Number: 4,783,532

[45] Date of Patent: Nov. 8, 1988

[54] PROCESS FOR PREPARING GRISEOLIC ACID DERIVATIVES

[75] Inventors: Masakatsu Kaneko; Misako Kimura; Yoshinobu Murofushi, all of Hiromachi, Japan

[73] Assignee: Sankyo Company Limited, Tokyo, Japan

[21] Appl. No.: 856,586

[22] Filed: Apr. 25, 1986

Related U.S. Application Data

[63] Continuation-in-part of Ser. No. 664,866, Oct. 25, 1984, Pat. No. 4,634,706.

[30] Foreign Application Priority Data

Oct. 28, 1983 [JP] Japan .................................. 58-202362
Apr. 27, 1985 [JP] Japan .................................. 60-91989

[51] Int. Cl.$^4$ .................... C07D 47/34; A61K 31/52
[52] U.S. Cl. ........................................ 544/277; 536/24; 536/26
[58] Field of Search ................ 544/277, 276; 536/24, 536/26

[56] References Cited

U.S. PATENT DOCUMENTS 4,460,765  7/1984  Naitr et al. ........................ 536/26
4,634,706  1/1987  Kaneko et al. ..................... 514/262

FOREIGN PATENT DOCUMENTS 0029329  5/1981  European Pat. Off. .

Primary Examiner—Nicholas S. Rizzo
Attorney, Agent, or Firm—Frishauf, Holtz, Goodman & Woodward

[57] ABSTRACT

Griseolic acid and dihydrodesoxygriseolic acid derivatives having an alkyl or aralkyl group as a substituent on the amino group at the 6-position are prepared by reacting the unsubstituted compound with a compound $R^7$-X (where $R^7$ is alkyl or aralkyl and X is halogen or sulfonyloxy). The group first substitutes and quaternizes the 1-nitrogen atom. The compound is then subjected to an appropriate combination of temperature and pH to cause ring cleavage, rearrangement and ring closure involving the 6-amino group and this quaternized 1-nitrogen to give a 6-alkylamino or 6-aralkylamino derivative.

26 Claims, No Drawings

PROCESS FOR PREPARING GRISEOLIC ACID DERIVATIVES

This application is a continuation-in-part application of U.S. Ser. No. 664,866 filed Oct. 25, 1984 (now U.S. Pat. No. 4,634,706 issued Jan. 6, 1987).

BACKGROUND TO THE INVENTION

The present invention relates to a novel process for preparing certain griseolic acid derivatives, which process enables the derivatives to be prepared in a high yield and by means of a simple process.

Griseolic acid is a nucleoside-type compound having an adenine base and two carboxylic acid groups. It was first disclosed in, inter alia, European Patent Specification No. 29,329A, and subsequently its structure was disclosed in U.S. Pat. No. 4,460,765.

Subsequently, copending U.S. patent application Ser. No. 664,866, filed on Oct. 25, 1984, which issued as U.S. Pat. No. 4,634,706, (and of which the present application is a continuation-in-part) disclosed a class of griseolic acid derivatives having activities at least as good as the natural product, griseolic acid, but having significantly lower toxicities. Certain of the compounds prepared by the process of the present invention are embraced by the general disclosure of said U.S. patent application, although only one such compound, $N^6$-methylgriseolic acid, is specifically disclosed. Other compounds prepared by the present invention are disclosed in copending U.S. patent application Ser. No. 854,418 filed Apr. 21, 1986 and entitled "Griseolic Acid Derivatives, Their Preparation and Their Use" now abandoned, and assigned to the present assignees.

The general class of griseolic acid derivatives, and especially the $N^6$-alkyl and $N^6$-aralkyl griseolic acid derivatives, are non-toxic and have a variety of valuable therapeutic activities arising primarily from their abilities to inhibit the activity of phosphodieserases (PDE) of, for example, cyclic adenosine monophosphate (cAMP). For example, they have shown the potential to be used as ameliorators of cerebral function, as angiocardiokinetic agents, as antithrombotic agents, as diuretics, as psychotropic and neurotropic agents, as smooth muscle relaxants and as anticancer agents.

However, it is always necessary that drugs should be capable of preparation at a cost at most commensurate with their therapeutic value and preferably as cheaply as possible. In any case, regardless of cost, where a drug is prepared by a multi-stage sequence of reactions or in low yield, there is always an increased danger that the drug may be contaminated by by-products which may be difficult or impossible to remove, and its value may thereby be degraded.

BRIEF SUMMARY OF INVENTION

It is, therefore, an object of the invention to provide a process for preparing certain griseolic acid derivatives, which process allows the derivatives to be obtained in a high yield and in very few reaction steps.

The compounds prepared by the process of the present invention are those compounds of formula (I):

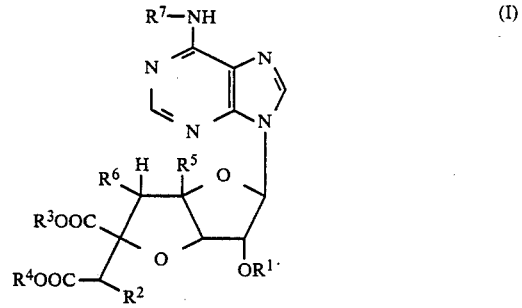

wherein:

$R^1$ represents a hydrogen atom or a hydroxy-protecting group;

$R^2$ represents a hydrogen atom, a hydroxy group or a protected hydroxy group;

$R^3$ and $R^4$ are independently selected from the group consisting of hydrogen atoms and carboxy-protecting groups;

$R^5$ and $R^6$ each represent hydrogen atoms or together represent an extra carbon-carbon bond between the carbon atoms to which they are attached; and $R^7$ represents an alkyl group or an aralkyl group; and salts thereof.

The process of the present invention comprises reacting a compound of formula (II):

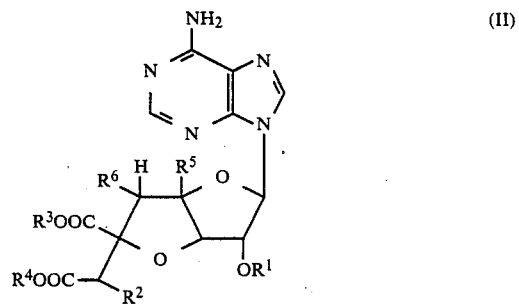

(in which $R^1$, $R^2$, $R^3$, $R^4$, $R^5$ and $R^6$ are as defined above) with a compound of formula (III):

$$R^7-X \qquad (III)$$

(in which: $R^7$ is as defined above; and X represents a halogen atom, a $C_1$-$C_6$ alkylsulfonyloxy group, a fluorinated $C_1$-$C_6$ alkylsulfonyloxy group, an arylsulfonyloxy group or a $C_1$-$C_6$ alkoxysulfonyloxy group), subjecting the aminopyrimidine ring of the product to ring cleavage, rearrangement and ring formation and, if desired, removing any protecting group and, if desired, salifying the product.

DETAILED DESCRIPTION OF INVENTION

The process of the present invention may be represented by the reaction shown in the following scheme:

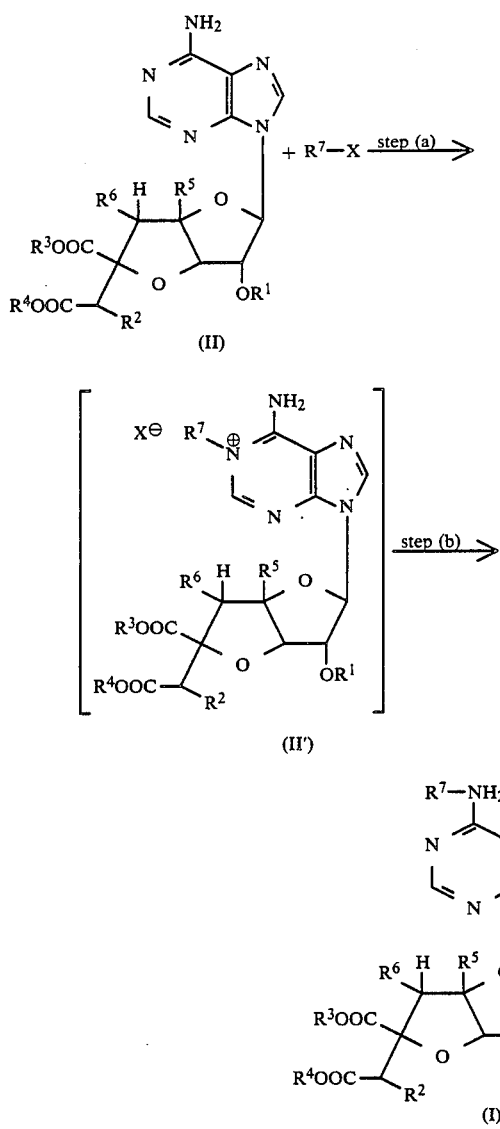

(in which $R^1$–$R^7$ and X are as defined above) followed, if necessary, by removal of protecting groups and/or salification.

Where $R^1$, $R^2$, $R^3$ or $R^4$ represents a protecting or protected group, the nature of such a group is not critical to the present invention. Where the final products of formula (I) are themselves to be used directly for therapeutic purposes, and where such a protecting group remains in the product of formula (I), it is, of course, necessary that the protecting group should not adversely affect the therapeutic value of the compounds (for example by either reducing their activity or increasing their toxicity to an unacceptable extent). However, where protecting groups are employed which do have such an adverse effect, they may easily be removed in the final step of the reaction sequence (as described in more detail hereafter). Alternatively, the protecting groups employed may be pharmaceutically acceptable and, in that case, the resulting compounds of formula (I) may be used directly for therapeutic purposes. Also, of course, if the compounds of formula (I) are themselves to be employed as intermediates in the preparation of yet other griseolic acid derivatives, it may be unnecessary to remove protecting groups and the nature of such protecting groups will not be critical.

Where $R^1$ or $R^2$ represents, respectively, a hydroxy-protecting group or a protected hydroxy group, examples of suitable hydroxy-protecting groups include aliphatic acyl groups, aromatic acyl groups, heterocyclic groups, tri-substituted silyl groups, lower alkyl groups, lower alkoxymethyl groups, substituted ethyl groups, aralkyl groups, lower alkoxycarbonyl groups, lower alkenyloxycarbonyl groups and protecting groups which are easily hydrolized in vivo.

Where the hydroxy-protecting group is an aliphatic acyl group, this is a carboxylic acyl group preferably having up to 6 carbon atoms and is more preferably an alkanoyl or alkenoyl group having up to 6, preferably up to 5, carbon atoms, which group may be unsubstituted or may have at least one substituent selected from the group consisting of halogen atoms, $C_1$–$C_4$ alkoxy groups and aryloxy groups. Examples include the acetyl, chloroacetyl, dichloroacetyl, trichloroacetyl, trifluoroacetyl, methoxyacetyl, propionyl, butyryl, (E)-2-methyl-2-butenoyl, isobutyryl, valeryl, isovaleryl and pivaloyl groups.

Where the hydroxy-protecting group is an aromatic acyl group, this is preferably an arylcarbonyl group, where the aryl part is preferably a $C_6$–$C_{14}$, more preferably $C_6$–$C_{10}$, carbocyclic aryl group, which may be unsubstituted or may have at least one substituent selected from the group consisting of halogen atoms, $C_1$–$C_4$ alkyl groups, $C_1$–$C_4$ alkoxy groups, aryl groups (which themselves are as defined in relation to the aryl groups of these arylcarbonyl groups), $C_1$–$C_4$ haloalkyl groups, $C_2$–$C_5$ alkoxycarbonyl groups, cyano groups and nitro groups. Examples of such aromatic acyl groups include the benzoyl, o-(dibromomethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl, o-nitrobenzoyl and α-naphthoyl groups.

Where the hydroxy-protecting group is a heterocyclic group, this is preferably such a group containing a single oxygen or sulfur hetero-atom and having 5 or 6 ring atoms (including the hetero-atom), for example a tetrahydrofuryl, tetrahydrothienyl, tetrahydropyranyl or tetrahydrothiopyranyl group. This may be unsubstituted or may have at least one substituent selected from the group consisting of the substituents defined above in relation to substituents on aryl groups, preferably halogen atoms or $C_1$–$C_4$ alkoxy groups. The tetrahydropyranyl, tetrahydrothiopyranyl, tetrahydrofuryl and tetrahydrothienyl groups are preferred. Examples of such groups include the tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups.

Where the hydroxy-protecting group is a tri-substituted silyl group, the substituents, which may be the same or different, are preferably $C_1$–$C_4$ alkyl groups and examples of such substituted silyl groups include the trimethylsilyl, triethylsilyl, isopropyldimethylsilyl, t-butyldimethylsilyl, diisopropylmethylsilyl, methyldi-t-butylsilyl and triisopropylsilyl groups.

Where the hydroxy-protecting groups are lower alkyl groups, these preferably have from 1 to 6 carbon atoms and may be straight or branched chain groups. Examples include the methyl, ethyl, propyl, isopropyl, butyl, isobutyl, sec-butyl, t-butyl, pentyl and hexyl groups.

Where the hydroxy-protecting group is a lower alkoxymethyl group, this may be a mono-alkoxymethyl or di-alkoxymethyl group and the alkoxy part is preferably a $C_1-C_6$, more preferably $C_1-C_4$, alkoxy group which may be unsubstituted or have at least one substituent selected from the group consisting of $C_1-C_4$ alkoxy groups and halogen atoms. Examples of such alkoxymethyl groups include the methoxymethyl, t-butoxymethyl, 2-methoxyethoxymethyl, 2,2,2-trichloroethoxymethyl and bis(2-chloroethoxy)methyl groups.

Where the hydroxy-protecting group is a substituted ethyl group, the ethyl group may have one or more, preferably from 1 to 3, substituents selected from the group consisting of $C_1-C_4$ alkoxy groups, $C_1-C_4$ alkyl groups, halogen atoms, $C_1-C_4$ alkylselenyl and arylselenyl groups (in which the aryl part is as defined in relation to the aryl parts of arylcarbonyl groups above). Examples include the 1-ethoxyethyl, 1-methyl-1-methoxyethyl, 1-isopropoxyethyl, 2,2,2-trichloroethyl and 2-phenylselenylethyl groups.

Where the hydroxy-protecting group is an aralkyl group, this may be a monoaryl-alkyl group, a diaryl-alkyl group or a triaryl-alkyl group. Each aryl part is preferably a $C_6-C_{14}$, more preferably $C_6-C_{10}$, carbocyclic aryl group and is as defined above in relation to the aryl groups of arylcarbonyl groups. It is preferably unsubstituted or has at least one substituent selected from the group consisting of $C_1-C_4$ alkyl groups, $C_1-C_4$ alkoxy groups, halogen atoms, nitro groups and cyano groups. The alkyl part is a straight or branched chain group preferably having from 1 to 4, more preferably 1 to 3 and most preferably 1 or 2, carbon atoms. Examples of such aralkyl groups include the benzyl, p-methoxybenzyl, o-nitrobenzyl, p-nitrobenzyl, p-halobenzyl (where the halo is preferably chloro, iodo, bromo or fluoro), p-cyanobenzyl, diphenylmethyl, triphenylmethyl, α-naphthyldiphenylmethyl and p-methoxyphenyldiphenylmethyl groups.

Where the hydroxy-protecting group is a lower alkoxycarbonyl group, this is preferably a $C_2-C_7$, more preferably $C_2-C_5$, alkoxycarbonyl group (i.e. the alkoxy part is $C_1-C_6$, more preferably $C_1-C_4$) and the alkoxy part may be unsubstituted or may have at least one substituent selected from the group consisting of halogen atoms and tri-substituted silyl group (e.g. as defined above in relation to the substituted silyl groups which may act as hydroxy-protecting groups). Examples of such alkoxycarbonyl groups include the methoxycarbonyl, ethoxycarbonyl, t-butoxycarbonyl, 2,2,2-trichloroethoxycarbonyl, isobutoxycarbonyl and 2-trimethylsilylethoxycarbonyl groups.

Where the hydroxy-protecting group is a lower alkenyloxycarbonyl group, the alkenyl part is preferably a $C_2-C_4$ alkenyl group and examples include the vinyloxycarbonyl and allyloxycarbonyl groups.

Where the hydroxy-protecting group is a group which is easily hydrolized in vivo, the group may fall within a number of different classes, including some classes which overlap with those hydroxy-protecting groups described above. In general, preferred such hydroxy-protecting groups include: the aralkyloxycarbonyl groups (in which the aralkyl part may be as defined above in relation to aralkyl groups which themselves serve as hydroxy-protecting groups), for example the benzyloxycarbonyl, p-methoxybenzyloxycarbonyl, 3,4-dimethoxybenzyloxycarbonyl, o-nitrobenzyloxycarbonyl and p-nitrobenzyloxycarbonyl groups; and the acyloxy-substituted alkoxycarbonyl, preferably methoxycarbonyl, groups, such as the pivaloyloxymethoxycarbonyl group.

Of these, we prefer the aliphatic acyl groups, the aromatic acyl groups and those protecting groups which are easily hydrolized in vivo.

Where $R^3$ or $R^4$ represents a carboxy-protecting group, examples include lower alkyl groups, lower haloalkyl groups, aralkyl groups and carboxy-protecting groups which are easily hydrolized in vivo.

Where $R^3$ and $R^4$ represents a lower alkyl group, this has from 1 to 6, preferably from 1 to 4, carbon atoms and may be a straight or branched chain group. Examples include the methyl, ethyl, propyl, isopropyl, butyl, isobutyl and t-butyl groups.

Where $R^3$ or $R^4$ represents a lower haloalkyl group, this likewise has from 1 to 6, preferably from 1 to 4, carbon atoms and at least one halogen substituent, although more halogen substituents may be present, up to complete perhalogenation. Examples include the 2,2,2-trichloroethyl, 2-chloroethyl, 2-bromoethyl, 2-iodoethyl, 2-fluoroethyl and 2,2-dibromoethyl groups.

Where $R^3$ or $R^4$ represents an aralkyl group, this may be a monoaryl-alkyl, diaryl-alkyl or triaryl-alkyl group, preferably a monoaryl-alkyl or diaryl-alkyl group. The aryl part is preferably a $C_6-C_{14}$ carbocyclic aryl group which may be unsubstituted or may have at least one substituent selected from the group consisting of nitro groups, $C_1-C_4$ alkyl groups, $C_1-C_4$ alkoxy groups, halogen atoms and $C_1$ or $C_2$ alkylenedioxy groups. Examples of such aralkyl groups include the benzyl, p-nitrobenzyl, o-nitrobenzyl, triphenylmethyl, diphenylmethyl, bis(o-nitrophenyl)methyl, 9-anthrylmethyl, 2,4,6-trimethylbenzyl, p-bromobenzyl, p-methoxybenzyl, 3,4,5-trimethoxybenzyl and piperonyl groups.

Where $R^3$ or $R^4$ represents a carboxy-protecting group which can easily be hydrolized in vivo, these may be selected from a wide range of different classes of groups, which are well-known to those skilled in the art. Examples include: aliphatic acyloxymethyl groups, in which the aliphatic acyl part is preferably a $C_2-C_6$ alkanoyl group, for example the acetoxymethyl, propionyloxymethyl, butyryloxymethyl or pivaloyloxymethyl groups; alkoxymethyl groups, where the alkoxy part is a $C_1-C_6$, preferably $C_1-C_4$, alkoxy group, and may be unsubstituted or have at least one substituent (if substituted, the substituent is preferably a single $C_1-C_4$ alkoxy substituent) and examples of such alkoxymethyl groups include the methoxymethyl, ethoxymethyl, propoxymethyl, isopropoxymethyl, butoxymethyl and 2-methoxyethoxymethyl groups: 1-alkoxycarbonyloxyethyl groups in which the alkoxy part is a $C_1-C_6$, preferably $C_1-C_4$, alkoxy group, for example the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl or 1-isobutoxycarbonyloxyethyl groups; the phthalidyl group; and the (2-oxo-5-methyl-1,3-dioxolen-4-yl)methyl group.

Of these carboxy-protecting groups, the alkyl groups, aralkyl groups and groups which are easily hydrolized in vivo are particularly preferred.

Where $R^7$ represents a lower alkyl group or an aralkyl group, these may be as defined above in relation to the equivalent carboxy-protecting groups which may be represented by $R^3$ or $R^4$.

X represents a halogen atom, a lower alkylsulfonyloxy group, a fluorinated lower alkylsulfonyloxy group, an arylsulfonyloxy group or a lower alkoxysulfonyloxy group.

Where X represents a halogen atom, this is preferably an iodine, chlorine or bromine atom.

Where X represents a lower alkylsulfonyloxy group, this is a $C_1$–$C_6$, preferably $C_1$–$C_4$, alkanesulfonyloxy group, for example a methanesulfonyloxy, ethanesulfonyloxy or propanesulfonyloxy group.

Where X represents a fluorinated lower alkylsulfonyloxy group, this is an alkylsulfonyloxy group as defined above which has at least one fluorine substituent, but which may have more than one fluorine substituent and may be, and preferably is, completely perfluorinated. Examples include the trifluoromethanesulfonyloxy and pentafluoroethanesulfonyloxy groups.

Where X represents an arylsulfonyloxy group, the aryl part may be as defined above in relation to the aryl part of the arylcarbonyl group which serves as a hydroxy-protecting group, and examples include the benzenesulfonyloxy and p-toluenesulfonyloxy groups.

Where X represents an alkoxysulfonyloxy group, the alkoxy part is a $C_1$–$C_6$, preferably $C_1$–$C_4$, alkoxy group and examples include the methoxysulfonyloxy, ethoxysulfonyloxy and propoxysulfonyloxy groups.

We particularly prefer that X should represent a halogen atom.

In Step (a) of the present of the invention, the griseolic acid or derivative thereof of formula (II) is subjected to alkylation or aralkylation with an alkylating or aralkylating agent (III) in an inert solvent. The nature of the solvent is not particularly critical, provided that it has no adverse effect upon the reaction. Examples of suitable solvents include: alcohols, such as methanol, ethanol, isopropanol, butanol and t-butanol; ethers, such as diethyl ether, tetrahydrofuran, dioxane or ethylene glycol dimethyl ether; nitriles, such as acetonitrile; amides, such as dimethylformamide, dimethylacetmaide or hexamethylphosphoric triamide; and sulfoxides, such as dimethyl sulfoxide. The preferred solvents are amides or sulfoxides.

The reaction will take place over a wide range of temperatures, but we prefer to carry out the reaction at a temperature of from 0° C. to 100° C., more preferably from room temperature to 70° C.

The time required for the reaction may vary widely, depending upon many factors, notably the reaction temperature and the natures of the solvents and reagents employed. In general, a period of from 30 minutes to 10 days will suffice. If, for example, the reaction is carried out at room temperature, it is generally complete within from 1 to 7 days; on the other hand, at 70° C., it will normally be complete within from 1 to 20 hours.

The intermediate product of formula (II') may be obtained from the reaction mixture by evaporating off the solvent under reduced pressure and then the product may be subjected to Step (b) without further isolation, in the same reaction vessel. Alternatively, if desired, the intermediate (II') may be isolated by conventional means before being subjected to Step (b).

In Step (b), the compound is subjected to a ring-opening, rearrangement and ring-closure reaction involving the pyrimidine ring and the free amino group.

In this step, the residue obtained from the alkylation or aralkylation reaction of Step (a) is dissolved or suspended in a suitable solvent and the pH of the resulting solution or suspension is adjusted or maintained at a value not less than 4, to effect the aforesaid ring-opening, rearrangement and ring-closure reactions. The pH value employed for these reactions is more preferably at least 5 and still more preferably at least 7.

Maintenance of the chosen pH value may be achieved, for example, either (1) by conducting the reactions in a buffer solution previously adjusted to an appropriate pH value or (2) by standing or heating the residue in an excess of an aqueous solution of an alkali metal or alkaline earth metal hydroxide or a solution containing an organic base in water or in a suitable organic solvent.

There is no particular limitation upon the nature of the buffer solution to be employed, provided that it is capable of maintaining an appropriate pH value throughout the reaction of Step (b). Any conventional buffer solution, for example an acetate, phosphate, borate, ammonium bicarbonate, phthalate or citrate buffer, may be used.

Examples of suitable alkali metal and alkaline earth metal hydroxides which may be used in the aqueous solution include sodium hydroxide, potassium hydroxide, lithium hydroxide and calcium hydroxide. Examples of suitable organic bases include, for example, lower alkylamines, such as monomethylamine, dimethylamine or trimethylamine.

In general, the pH of the reaction solution is preferably maintained within the range from 4 to 12, although higher pH values may also be employed.

There is no particular limitation on the nature of the solvent employed in this reaction, provided that it does not interfere with the reactions. Suitable solvents include, for example: water; alcohols, such as methanol, ethanol or propanol; and other water-miscible solvents, such as acetone, tetrahydrofuran, dioxane, dimethylformamide or dimethyl sulfoxide. A single such solvent or a mixture of any two or more thereof may be employed. In some cases, the organic base may also act as the reaction solvent.

The reaction may take place over a wide range of temperatures, for example from 0° C. to 150° C., more preferably from 20° C. to 100° C. The temperature chosen may depend upon various factors. For example, heating may be preferably when the reaction is carried out at a pH value within the range from 4 to 10; on the other hand, the reaction will generally proceed satisfactorily at ambient temperature at a pH of 10 or above.

The time required for the reaction may vary widely, depending upon many factors, notably the nature of the substrates, the reaction temperature and the pH and nature of the buffer or other medium used, especially the temperature and pH; however, within the preferred ranges indicated above, a period of from 5 minutes to 50 hours will normally suffice.

After completion of the reaction, the resulting compound of formula (I) may be recovered from the reaction mixture by conventional means, for example any one or any appropriate combination of the following steps: adjustment of the pH of the reaction mixture; concentration of the reaction mixture, e.g. by evaporating off the solvent under reduced pressure; separating, e.g. by filtration, of the precipitate obtained from recrystallization of the reaction residue; or, if no crystalline precipitate is thereby produced, extracting the mixture with a water-immiscible solvent and then evaporating the solvent from the extract. If desired, the resulting product may be further purified by conventional techniques, for example recrystallization or the various chromatography techniques such as column chromatography or preparative thin layer chromatography.

Where the resulting compound of formula (I) contains a hydroxy-protecting group and/or a carboxy-protecting group, such protecting groups may, if desired, be removed in a step following Step (b). The nature of the process employed to remove these protecting groups will vary depending upon the nature of the protecting group, as is well-known in the art.

For example, where a trialkylsilyl group is employed as a hydroxy-protecting group, it may be removed by treating the compound of formula (I) with a compound which produces fluoride anions, for example tetrabutylammonium fluoride. The reaction is preferably effected in the presence of a solvent, the nature of which is not critical, provided that it has no adverse effect upon the reaction; suitable solvents include ethers, such as tetrahydrofuran or dioxane. The reaction temperature is not particularly critical, and we generally find it convenient to carry out the reaction at about room temperature, at which temperature a period of from 10 to 18 hours is normally required.

Where an aralkyloxycarbonyl group or aralkyl group is employed as a hydroxy-protecting group, it may be removed by contacting the compound with a reducing agent. Suitable reducing agents include, for example, hydrogen in the presence of a catalyst (e.g. palladium-on-activated carbon or platinum) or an alkali metal sulfide (such as sodium sulfide or potassium sulfide). These reactions are preferably carried out in the presence of a solvent, the nature of which is not critical, provided that it has no adverse effect upon the reaction. Examples of preferred solvents include: alcohols, such as methanol or ethanol; ethers, such as tetrahydrofuran or dioxane; fatty acids, such as acetic acid; and mixtures of one or more of these organic solvents with water. The reaction will take place over a wide range of temperatures, the preferred temperature depending upon the nature of the reducing agent. For example, in the case of catalytic reduction, room temperature is preferred. In the case of reduction employing alkali metal sulfides or similar reducing agents, a temperature of about room temperature or below, e.g. down to 0° C., is normally preferred. The time required for the reaction may vary widely, depending upon many factors, notably the natures of the starting materials and reducing agents, and the reaction temperature; however, a period of from 5 minutes to 12 hours will normally suffice.

Where a lower alkyl group, lower aliphatic acyl group, aromatic acyl group or alkoxycarbonyl group is employed as the hydroxy-protecting group, it may be removed by treating the compound of formula (I) with a base in the presence of an aqueous solvent. There is no particular limitation on the nature of the solvent to be employed and any solvent commonly used in hydrolysis reactions may equally be used in this reaction. Examples of preferred solvents include water itself and mixtures of water with one or more organic solvents, for example: alcohols, such as methanol, ethanol or propanol; and esters, such as tetrahydrofuran or dioxane. Equally, there is no particular limitation on the nature of the base to be employed, and any base commonly used in hydrolysis reactions may be employed, provided that it does not adversely affect other functional groups of the compound. Examples of preferred bases include: alkali metal carbonates, such as sodium carbonate or potassium carbonate; and ammonia in water or in a suitable organic solvent. The reaction will take place over a wide range of temperatures, but we generally prefer to employ a temperature of about room temperature or below, e.g. down to 0° C. The time required for the reaction will vary, depending upon many factors, notably the nature of the starting materials and the reaction temperature, but a period of from 1 to 6 hours will normally suffice.

Where a heterocyclic group (e.g. a tetrahydropyranyl, tetrahydrothiopyranyl, tetrahydrofuryl or tetrahydrothienyl group), an alkoxymethyl group or a substituted ethyl group is employed as the hydroxy-protecting group, it may be removed by treating the compound of formula (I) with an acid in a solvent. There is no particular limitation on the nature of the acid and examples include hydrochloric acid, a mixture of acetic acid with sulfuric acid, or a mixture of p-toluenesulfonic acid with acetic acid. There is equally no particular limitation on the nature of the solvent, provided that it has no adverse effect upon the reaction. Examples of preferred solvents include: alcohols, such as methanol or ethanol; ethers, such as tetrahydrofuran or dioxane; and mixtures of water with one or more of these organic solvents. The reaction will take place over a wide range of temperatures, but we generally prefer to carry out the reaction at a temperature within the range from 0° to 50° C. The time required for the reaction will vary, depending upon many factors, notably the nature of the starting materials and acids and the reaction temperature, but a period of from 10 minutes to 18 hours will normally suffice.

Where an alkenyloxycarbonyl group is employed as the hydroxy-protecting group, it may be removed by treating the compound with a base in the presence of an aqueous solvent, under the same conditions as employed for removal of lower alkyl, aliphatic acyl, aromatic acyl and alkoxycarbonyl groups. If the group is an allyloxycarbonyl group, it can also simply be removed by using palladium and triphenylphosphine or nickel tetracarbonyl, and this has the advantage that very few side reactions may occur.

Depending upon the nature of the respective hydroxy-protecting groups and carboxy-protecting groups, some of the reactions employed above may simultaneously remove carboxy-protecting groups, as described below.

After completion of any of the above reactions, the desired compounds may be recovered from the reaction mixture by conventional means, and, if required, may be further purified by such conventional techniques as recrystallization or the various chromatography techniques, particularly preparative thin layer chromatography or column chromatography.

Where a lower alkyl group is employed as a carboxy-protecting group, it may be removed by treating the compound of formula (I) with a base in the presence of an aqueous solvent. The reaction is carried out under the same conditions as are employed for elimination of a hydroxy-protecting group, when that group is a lower alkyl, aliphatic acyl, aromatic acyl or alkoxycarbonyl group; such groups may, therefore, be removed simultaneously.

Where an aralkyl or lower haloalkyl group is employed as a carboxy-protecting group, it may be removed by contacting the compound of formula (I) with a reducing agent, for example zinc in acetic acid. In the case of the aralkyl group, other reducing agents include hydrogen in the presence of a catalyst and alkali metal sulfides (such as potassium sulfide or sodium sulfide); such a reaction may be carried out under the same conditions as are employed for removing a hydroxy-protecting group when that group is an aralkylcarbonyl or aralkyl group; such as protecting group may, therefore, be removed simultaneously.

Where an alkoxymethyl group is employed as the carboxy-protecting group, it may be eliminated by treating the compound with an acid. The reaction is carried out under the same conditions as are employed for eliminating a hydroxy-protecting group when that group is an alkoxymethyl or substituted ethyl group; such a protecting group may, therefore, be removed simultaneously.

After completion of these reactions, the desired compounds may be recovered from the reaction mixture by conventional means. For example, one suitable recovery technique comprises: filtering off insoluble materials, if any; washing the resulting organic solvent solution containing the desired compound with water; drying the solution; and then distilling off the solvent. The resulting residue may, if desired, be further purified by various conventional techniques, such as recrystallization or the various chromatography techniques, particularly preparative thin layer chromatography or column chromatography.

The order in which the hydroxy-protecting groups and carboxy-protecting groups are removed is not critical and these may be removed in any desired sequence or simultaneously.

Also, if desired, where the resulting product contains a free hydroxy and/or carboxy group, one or more of these may be protected by a group which can easily be hydrolized in vivo. This reaction may be carried out by conventional methods well-known to those skilled in the art, the precise method chosen depending upon the nature of the protecting group which is to be introduced.

For example, a carboxy group may be protected by conversion to the corresponding ester capable of easy hydrolysis in vivo by reacting the acid with a halide corresponding to the protecting group which it is desired to introduce, for example with: an aliphatic acyloxymethyl halide, such as acetoxymethyl chloride, propionyloxymethyl bromide or pivaloyloxymethyl chloride; a lower alkoxycarbonyloxyethyl halide, such as 1-methoxycarbonyloxyethyl chloride or 1-ethoxycarbonyloxyethyl iodide; a phthalidyl halide, e.g. chloride, bromide or iodide; or a (2-oxo-5-methyl-1,3-dioxolen-4-yl)methyl halide, e.g. chloride, bromide or iodide. The reaction is preferably effected in the presence of a solvent, the nature of which is not critical, provided that it has no adverse effect upon the reaction. Preferred solvents are such polar solvents as dimethylformamide. The reaction will take place over a wide range of temperatures, but we generally find it convenient to carry out the reaction at a temperature in the range from 0° to 100° C. The time required for the reaction may vary widely, depending upon many factors; however, under the conditions suggested, a period of from 30 minutes to 10 hours will normally suffice.

The compounds of formula (II) used as starting materials in the process of the invention may be prepared by a variety of reactions starting either from griseolic acid itself [which has the formula (A) shown below] or dihydrodesoxygriseolic acid [which has the formula (B) shown below]:

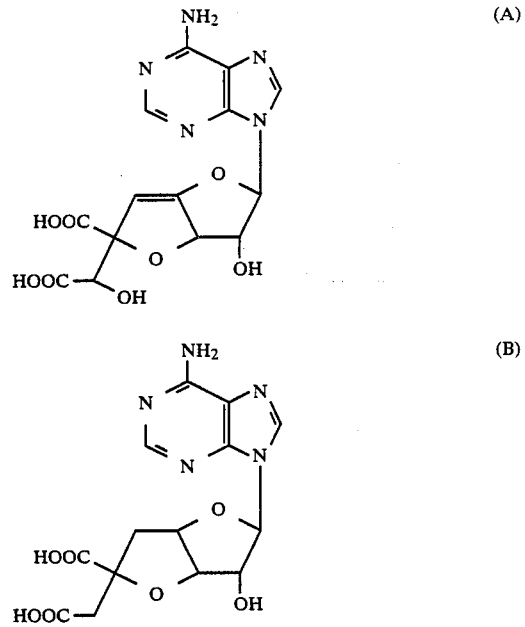

As already described above, griseolic acid is a known compound disclosed, for example, in European Patent Specification No. 29,329 or in U.S. Pat. No. 4,460,765. Dihydrodesoxygriseolic acid was disclosed in European Patent Publication No. 0162715, published after the priority hereof. Both griseolic acid and dihydrodesoxygriseolic acid may be produced by cultivating suitable microorganisms of the genus Streptomyces, especially *Streptomyces griseoaurantiacus* SANK 63479 (deposited on Oct. 9, 1979 at the Fermentation Research Institute, Agency of Industrial Science and Technology, Japan, whence it is available under the Accession No. FERM-P5223, and on Oct. 22, 1980 at the Agricultural Research Service, Peoria, U.S.A., whence it is available under the Accession No. NRRL 12314). Full details of the characteristics of *Streptomyces griseoaurantiacus* SANK 63479 are given in European Patent Publication No. 29,329A and in U.S. Pat. No. 4,460,765.

The various methods employed for preparing the compounds of formula (II) may be summarized by the following reaction scheme:

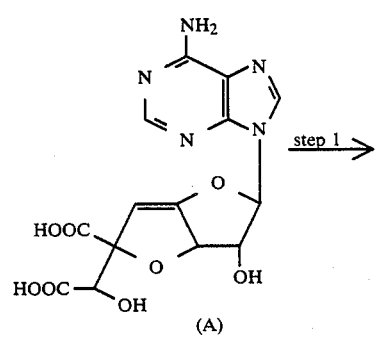

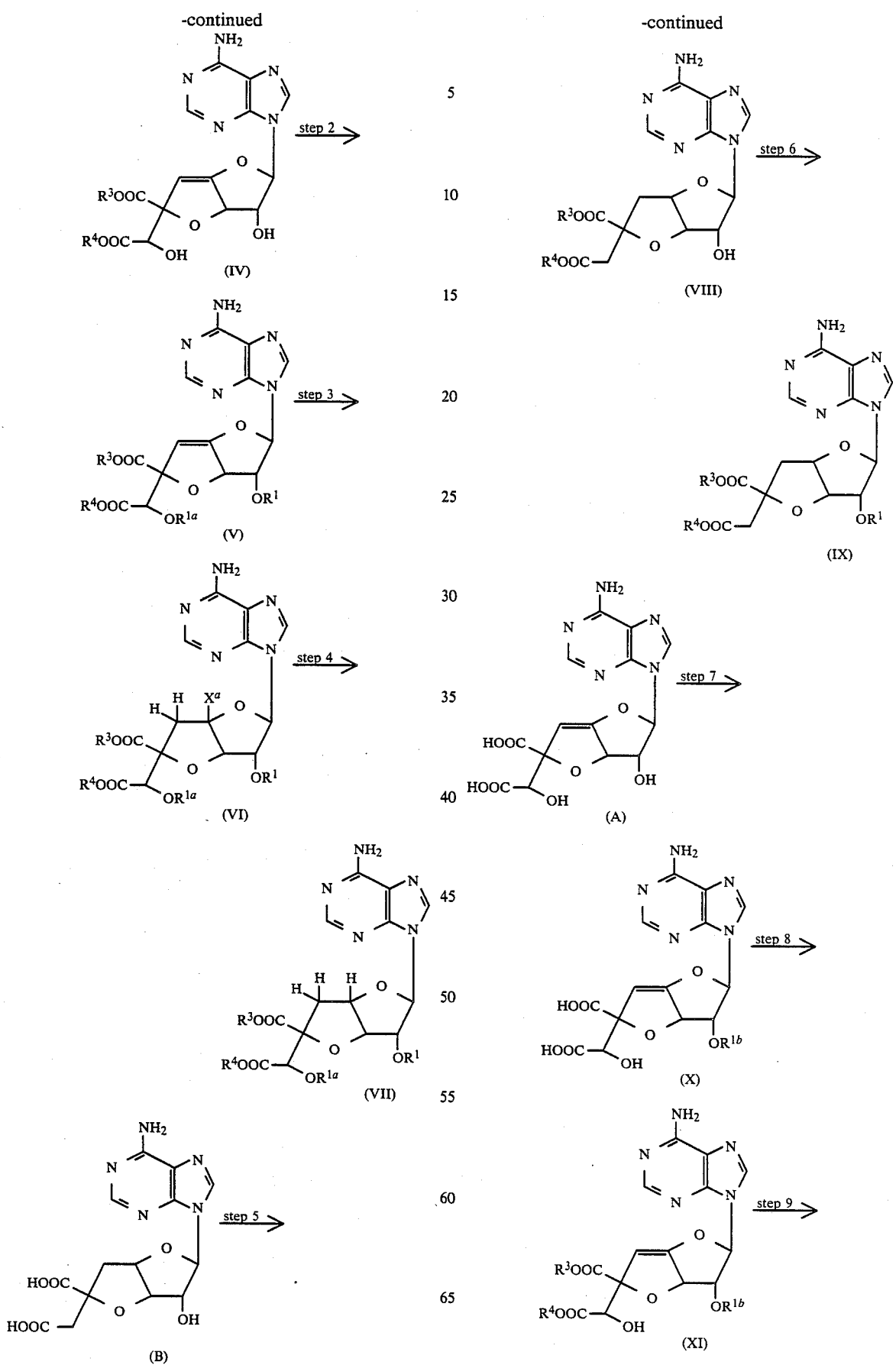

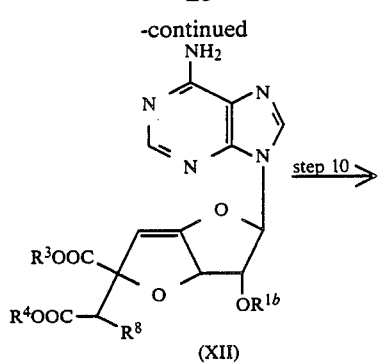

(XII)

(XIII)

In the above formulae, $R^1$, $R^3$ and $R^4$ are as defined above. $R^{1a}$ represents any of the groups defined above for $R^1$ and may be the same as or different from $R^1$. $R^{1b}$ represents an acyl group, including any of the acyl groups hereinbefore defined in relation to $R^1$. $R^8$ represents an alkylsulfonyloxy group, a fluorinated lower alkylsulfonyloxy group or an arylsulfonyloxy group, and examples of such groups are given previously in relation to the same groups which may be represented by X. $X^a$ represents a halogen atom, e.g. any one of those halogen atoms given previously in relation to X.

The various reactions involved in this reaction scheme may be carried out as described below:

Protection of Carboxy Groups (Steps 1, 5 and 8)

In these reactions, the free carboxy groups of the griseolic acid of formula (A), the dihydrodesoxygriseolic acid of formula (B) or the griseolic acid derivative of formula (X) are, in Steps 1, 5 and 8, respectively, protected by protecting groups $R^3$ and $R^4$, to give compounds of formulae (IV), (VIII) or (XI), respectively. This reaction may be effected by reacting the compound of formula (A), (B) or (X) with a diazo compound, such as diazomethane or diphenyldiazomethane, or a p-tolyltriazene derivative, such as N-methyl-p-tolyltriazene. The reaction is preferably effected in the presence of a solvent, the nature of which is not critical, provided that it has no adverse effect upon the reaction and that it is capable of dissolving, at least to some degree, the starting materials employed in the reaction. Examples of suitable solvents include: ketones, such as acetone; ethers, such as tetrahydrofuran; amides, such as dimethylformamide; and mixtures of water with one or more of these organic solvents.

The reaction will take place over a wide range of temperatures, and there is no particular limitation on the precise temperature chosen. We generally find it convenient to carry out the reaction at a temperature in the range from $-20°$ C. to $+50°$ C. The time required for the reaction may vary widely, depending upon many factors, notably the reaction temperature, but, for example, if the reaction is carried out, as is preferred, at room temperature, a period of from 1 to 24 hours will normally suffice.

If, instead of the free acids of formula (A), (B) or (X), the corresponding alkali metal salts are employed, this protection step may be achieved by reacting the alkali metal salt with a halide, for example methyl iodide, benzyl bromide, acetoxymethyl bromide, 1-methoxycarbonyloxy iodide or (2-oxo-5-methyl-1,3-dioxolen-4-yl)methyl bromide, by conventional means, to introduce the corresponding carboxy-protecting groups.

Protection of Hydroxy Groups (Steps 2 and 6)

In these reactions, the hydroxy groups of the compound of formula (IV) or the hydroxy group of the compound of formula (VIII) may be protected by reacting the compound with a corresponding acyl halide (such as acetyl chloride or benzoyl bromide) or a corresponding acid anhydride (such as acetic anhydride) or with another halide corresponding to the protecting group $R^1$ or $R^{1a}$ (such as trimethylsilyl iodide) in the presence of a base to give the protected compound of formula (V) or (IX), respectively. The reaction is preferably effected in the presence of a solvent, the nature of which is not critical, provided that it has no adverse effect upon the reaction. In general, we prefer to use pyridine as the solvent, as this has the advantage of also acting as the base.

The reaction will take place over a wide range of temperatures, although we generally prefer to use a relatively low temperature, e.g. from $-20°$ C. to room temperature, in order to control side reactions. The time required for the reaction will vary widely, depending upon many factors, notably the reaction temperature; however, at temperatures within the preferred range, a period of from 1 to 15 hours will normally suffice.

Alternatively, the compound of formula (IV) or (VIII) can be reacted with an unsaturated heterocyclic compound, such as dihydropyran, in the presence of an acid (e.g. hydrochloric acid) to give a protected compound (V) or (IX) protected with a corresponding protecting group.

Addition of a Hydrogen Halide Across the Double Bond (Step 3)

In this step, the compound of formula (V) is reacted with a hydrogen halide $HX^a$ to add the hydrogen halide across the double bond and give the compound of formula (VI). The reaction is preferably effected in the presence of a solvent, the nature of which is not critical, provided that it has no adverse effect upon the reaction and that it can dissolve the starting materials, at least to some degree. Preferred solvents are organic acids, such as acetic acid. The hydrogen halide employed is preferably hydrogen chloride, hydrogen bromide or hydrogen iodide. The reaction will take place over a wide range of temperatures, e.g. from 0° C. to 100° C., preferably either from 0° C. to room temperature or from 80° C. to 100° C. The time required for the reaction will vary, depending upon many factors, notably the reaction temperature and the natures of the solvents and reagents, but a period of from 1 to 72 hours will normally suffice.

If the hydroxy-protecting groups $R^1$ or $R^{1a}$ are capable of removal under acidic conditions (e.g. the trimethylsilyl or tetrahydropyranyl groups), they may be removed in the course of this step. In such a case, it may

Hydrodehalogenation (Step 4)

In this step, the halogen atom at the 4'-position of the compound of formula (VI) is reduced to give the compound of formula (VII). This reacton may be carried out either by using a tri-substituted tin hydride (such as tributyltin hydride) in an aromatic hydrocarbon (such as benzene) or by using zinc powder in a lower aliphatic carboxylic acid (such as acetic acid) or an alcohol (such as methanol or ethanol). The reaction is preferably conducted either: using tributyltin hydride at the boiling point of the solvent for a period of from 2 to 10 hours; or using zinc powder at a temperature of from room temperature to 100° C. for a period of from 2 to 20 hours.

Selective Acylation of the 2'-Hydroxy Group (Step 7)

In this step, the hydroxy group at the 2'-position of griseolic acid (A) is selectively acylated to give the compound of formula (X). This reaction may be effected either: by adding an acylating agent to griseolic acid whilst the pH of the reaction solution is maintained at a value of from 10 to 13 by means of a base, such as sodium hydroxide; or by adding an acylating agent to a solution of griseolic acid in a buffer solution of pH 10-13. The reaction is preferably effected in the presence of a solvent, the nature of which is not critical, provided that it has no adverse effect upon the reaction; water-immiscible solvents are preferred. The reaction will take place over a wide range of temperatures, although we generally prefer to employ a temperature of from $-20°$ C. to $+50°$ C. The time required for the reaction may vary widely, depending upon many factors, notably the reaction temperature and the natures of the solvents, bases and reagents, but a period of from 1 to 10 hours will normally suffice.

Sulfonylation of the 7'-Hydroxy Group (Step 9)

In this step, the hydroxy group at the 7'-position of the compound of formula (XI) is sulfonylated, to give the compound of formula (XII). The reaction is preferably effected using a sulfonyl halide, such as methanesulfonyl chloride, p-toluenesulfonyl chloride or trifluoromethanesulfonyl chloride, in the presence of an acid-binding agent, such as pyridine or dimethylaminopyridine. The reaction is preferably effected in the presence of a solvent, the nature of which is not critical, provided that it has no adverse effect upon the reaction. Preferred solvents are halogenated hydrocarbons, especially halogenated aliphatic hydrocarbons, such as methylene chloride or chloroform. The reaction will take place over a wide range of temperatures, although we generally prefer to employ a relatively low temperature, e.g. from $-10°$ C. to room temperature. In order to control side reactions. The time required for the reaction may vary widely, depending upon many factors, notably the reaction temperature and the natures of the reagents, but a period of from 1 to 20 hours will normally suffice.

Reduction of 7'-Sulfonyloxy Group (Step 10)

In this reaction, the compound of formula (XIII) is prepared by replacing the sulfonyloxy group at the 7'-position of compound of formula (XII) by a halogen atom and then replacing this halogen atom by a hydrogen atom.

Replacement of the sulfonyloxy group by a halogen atom is effected by reacting the compound of formula (XII) with an anhydrous lithium halide. The reaction is preferably effected in the presence of a solvent, the nature of which is not critical, provided that it has no adverse effect upon the reaction. Examples of preferred solvents are such polar solvents as: acid amides, such as dimethylformamide or hexamethylphosphoric triamide; sulfoxides, such as dimethyl sulfoxide; and alkyl phosphates, such as triethyl phosphate. The reaction will take place over a wide range of temperatures and the precise temperature chosen is not critical. We generally find it convenient to employ a temperature in the range from 0° to 150° C. The time required for the reaction may vary, depending on many factors, notably the temperature and nature of the reagents; however, under the conditions suggested above, a period of from 1 to 10 hours will normally suffice.

In a next stage, the halogen atom is replaced by a hydrogen atom. This may be effected by means of any conventional reducing (hydrogenating) agent capably of replacing a halogen atom by a hydrogen atom. It is preferably effected using zinc/aqueous acetic acid and may be carried out by adding zinc powder to a solution of the halogenated compound of formula (XII) in aqueous acetic acid. The reaction will take place over a wide range of temperatures, although a temperature from 0° C. to 150° C. is preferred. The time required for the reaction will vary, depending upon many factors, notably the reaction temperature and the nature of the reagents, but a period of from 1 to 10 hours will normally suffice.

In addition, if desired, the group $R^{1b}$ may be removed by conventional alkaline hydrolysis (for example with sodium hydroxide in aqueous methanol) and then the resulting hydroxy group may, if desired, be reprotected, as described in Step 2.

The process of the present invention is further illustrated by the following Examples. Of the starting materials, griseolic acid may be prepared as described in aforementioned U.S. Pat. No. 4,460,765, dimethyl griseolate may be prepared by simple esterification of griseolic acid (e.g. as described in Steps 1, 5 and 8 above) and dihydrodesoxygriseolic acid may be prepared as described in the subsequent Preparation.

EXAMPLE 1

$N^6$-Methylgriseolic acid (a) 2 ml of methyl iodide were added to a solution of 1.63 g of dimethyl griseolate in 20 ml of dimethylformamide, and the mixture was stirred at room temperature for 48 hours in a sealed vessel. The solvent was then evaporated off under reduced pressure, and the residue was mixed with 10 ml each of acetone and toluene, and then the solution was concentrated by evaporation under reduced pressure. This operation was repeated a total of three times to give a residue, which was dissolved in 30 ml of water and adjusted to a pH value of 5.7 with a 0.1N aqueous solution of sodium hydroxide. The mixture was heated at 100° C. for 2.5 hours, while at 30 minutes intervals the pH was re-adjusted to 5.7. The reaction mixture was then evaporated under reduced pressure to reduce the volume to 10 ml. 10 ml of a 2N aqueous solution of sodium hydroxide were added to the concentrate and the mixture was allowed to stand for 2 hours. The mixture was then adjusted to a pH value of 2.3 and purified by chromatography using an RP-8 prepacked column (Merck). The main fractions were collected, lyophilized and recrystallized from water, to give 690 mg of the title compound.

(b) 25 ml of methyl iodide were added to a solution of 18.95 g of griseolic acid in 230 ml of dimethylformamide, and the mixture was stirred at room temperature for 42 hours in a sealed vessel. At the end of this time, the solution was concentrated by evaporation under reduced pressure. The residue was then mixed with 70 ml each of ethanol and toluene and again concentrated by evaporation under reduced pressure. This operation was repeated a total of four times to give a residue, to which 300 ml of ethanol were added. The mixture was again concentrated by evaporation under reduced pressure to give a powdery residue. A suspension of the residue in 800 ml of ethyl acetate was ultrasonically treated to give a powder, and was then allowed to stand overnight in a refrigerator. Filtration of the suspension yielded 27.2 g of a pale yellow powder. The powder was dissolved in a 1N aqueous solution of sodium hydroxide, and adjusted to a pH value of 7.0. Water was added to the solution to give a total volume of 200 ml. A mixture of the solution with 50 ml of a 0.5M phosphate buffer (pH 7.0) was heated for 3 hours under reflux, and then the pH of the mixture was adjusted with a 1N aqueous solution of sodium hydroxide to a value of 7.0. The mixture was heated under reflux for 2 hours, and then its pH was adjusted with concentrated hydrochloric acid to a value of 2.3. It was then treated with activated carbon, concentrated by evaporation under reduced pressure to an amount of about 130 ml, and then subjected to column chromatography using an RP-8 prepacked column (Merck), eluted with water containing 3% v/v acetonitrile. The main fractions were collected, concentrated and recrystallized from water to give 12.73 g of the title compound. Concentration and cooling of the mother liquor yielded an additional 2.01 g of the title compound.

Ultraviolet Absorption Spectrum ($H_2O$) $\lambda_{max}$ nm ($\epsilon$): 265 (17200).

Nuclear Magnetic Resonance Spectrum [$(CD_3)_2SO$]$2\delta$ ppm: 4.52 (1H, singlet): 4.60 (1H, doublet, J=6.0 Hz); 5.10 (1H, doublet, J=3.0 Hz); 6.08 (1H, doublet of doublets, J=3.0 & 6.0 Hz); 6.53 (1H, singlet); 8.31 (1H, singlet); 8.35 (1H, singlet).

EXAMPLE 2

$N^6$-Methyl-7'-desoxy-4'$\alpha$,5'-dihydrogriseolic acid 1 ml of methyl iodide was added to a solution of 100 mg of 7'-desoxy-4'$\alpha$,5'-dihydrogriseolic acid in 20 ml of dimethylformamide, and the mixture was allowed to stand at room temperature for 24 hours in a sealed vessel. The solvent was distilled off under reduced pressure to give a residue. 10 ml each of acetone and toluene were added to the residue and the mixture was concentrated by evaporation under reduced pressure. This operation was repeated twice. A solution of the resulting residue in 20 ml of a 0.5M phosphate buffer of pH 7.0 was stirred for 3 hours under reflux, to give a reaction mixture which was purified by column chromatography using an RP-8 prepacked column (Merck), eluted with water containing 3% v/v acetonitrile, followed by lyophilizing the main fractions to give 67 mg of the title compound as a white powder.

Ultraviolet Absorption Spectrum ($\epsilon$) $\lambda_{max}$: pH 1.0 262 nm (17700). $H_2O$ 264 nm (16700). pH 13 266 nm (17100).

Nuclear Magnetic Resonance Spectrum [$(CD_3)_2SO+D_2O$]$\delta$ ppm: 2.28–2.31 (2H, multiplet); 2.80–3.03 (5H, multiplet); 4.37–4.46 (3H, multiplet); 6.16 (1H, singlet); 8.26 (1H, doublet); 8.28 (1H, singlet).

EXAMPLE 3

$N^6$-Methylgriseolic acid 6 ml of methyl iodide and 250 mg of sodium sulfite were added to a solution of 3.8 g of griseolic acid in 50 ml of dimethylformamide, and the mixture was heated at 40° C. for 17 hours, whilst stirring. The solvent was then distilled off under reduced pressure to give a residue. 20 ml each of ethanol and toluene were added to the residue, and the mixed solvent was distilled off under reduced pressure. This operation was repeatd three times. 50 ml of a 1N aqueous solution of sodium hydroxide were added to the residue and the mixture was allowed to stand at room temperature for 4 days. The mixture was then adjusted to a pH value of 2.3 with concentrated hydrochloric acid and allowed to stand for 1.5 hours whilst ice-cooling. The crystals which precipitated were collected by filtration, to yield 3.0 g of the title compound as crude crystals. The filtrate was then subjected to column chromatography using 200 ml of a CHP20 resin. After washing with 1.5 liter of water, the main fractions were eluted with water containing 3% v/v acetonitrile, followed by lyophilizing to give 0.9 g of the title compound. The above crude crystals and the substance lyophilized were together dissolved in 20 ml of a 1N aqueous solution of sodium hydroxide and the mixture was weakly acidified with 5 ml of a 1N aqueous solution of hydrochloric acid, treated with active carbon, and then further acidified with 15 ml of a 1N aqueous solution of hydrochloric acid. It was then allowed to stand at 5° C. overnight. The crystals which precipitated were collected and dried over phosphorus pentoxide to give 2.90 g of the title compound, whose properties were the same as those of the product of Example 1.

EXAMPLE 4

$N^6$-Methyl-7'-desoxy-4'$\alpha$,5'-dihydrogriseolic acid 1 ml of methyl iodide and 7 mg of sodium sulfite were added to a solution of 100 mg of 7'-desoxy-4'$\alpha$,5'-dihydrogriseolic acid in 20 ml of dimethylformamide, and the mixture was heated at 40° C. for 17 hours, whilst stirring. The solvent was then distilled off under reduced pressure to give a residue. 10 ml each of acetone and toluene were added to the residue and the mixed solvent was distilled off under reduced pressure. This operation was repeated three times. 1.5 ml of a 1N aqueous solution of sodium hydroxide were added to the residue and the mixture was allowed to stand at room temperature for 4 days. The mixture was then adjusted to a pH value of 2.3 with concentrated hydrochloric acid and purified by chromatography using an RP-8 prepacked column (Merck) (eluent:water containing 3% v/v acetonitrile). The main fractions were collected and lyophilized to give 80 mg of the title compound as a white powder, whose properties were the same as those of the product of Example 2.

PREPARATION

Dihydrodesoxygriseolic acid 30 liters of a medium having a pH of 7.0 before sterilization and the following composition (percentages are w/v) were prepared:
Glucose 5%
Soybean Meal 1%
Yeast Extract 0.1%
Polypeptone 0.4%
Meat Extract 0.4%
Sodium Chloride 0.25%
Calcium Carbonate 0.5%
Water to 100%

15 liters of this medium were charged into each of two 30 liter jar fermenters, which were then sterilized under pressure at 120° C. for 30 minutes. The culture medium was cooled, and then 150 ml (1% by volume) of a culture broth of Streptomyces griseoaurantiacus SANK 63479 (which had previously been incubated in the medium described above by means of a rotatory shaking cultivator at 28° C. for 72 hours) were inoculated into each fermenter. Cultivation was then carried out at 28° C. for 96 hours under aeration at the rate of 15 liters per minute and with agitation at the rate of 200 rpm.

The two culture broths were then filtered to remove the mycelial cake and the combined filtrates (pH 7.0), in a total volume of 28 liters, were passed through a column of Diaion HP 20 (a trademark for an ion-exchange resin produced by Mitsubishi Chemical Industries Ltd.) and then adsorbed on a column of activated charcoal. This column was washed with water and then the adsorbed material was eluted with a 60:40 by volume mixture of acetone and water. The acetone was evaporated from the resulting solution under reduced pressure and the remaining aqueous solution was concentrated by evaporation under reduced pressure and then lyophilized, to give 150 mg of a crude powder.

This crude powder was dissolved in a small amount of distilled water and then adsorbed on Dowex 1×4 (Cl⁻ form, a trademark for an ion-exchange resin produced by the Dow Chemical Company). At this stage, the product was a mixture of griseolic acid and dihydrodesoxygriseolic acid. This mixture was subjected to gradient elution with a sodium chloride gradient to separate the two components and then the eluate was subjected to column chromatography through Sephadex LH-20 (a trademark for a product of Pharmacia Co) and the dihydrodesoxygriseolic acid was eluted with water. The fractions containing this substance were combined and their pH was adjusted to a value of 2.5 by the addition of 1N aqueous hydrochloric acid. The product was then adsorbed on a column of Diaion HP 20, washed with water and then eluted with a 60:40 by volume mixture of acetone and water. The eluate was left to stand overnight at 4° C., whereupon the dihydrodesoxygriseolic acid separated out as plates. These were separated from the liquor, giving a total of 1.87 mg of dihydrodesoxygriseolic acid, as white plates melting at 160° C. (with decomposition, accompanied by a brown discoloration). This compound gave a single spot on silica gel thin layer chromatography (silica gel Art. 5715, a product of Merck & Co. Inc.).

We claim:

1. A process for preparing compounds of formula (I):

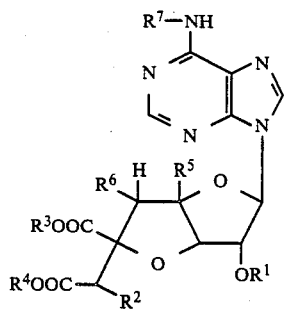

wherein:
$R^1$ represents a hydrogen atom or a hydroxy-protecting group selected from the group consisting of $C_2$-$C_6$ aliphatic acyl; benzoyl; benzoyl having a halogen, $C_1$-$C_4$ alkyl, $C_1$-$C_4$ alkoxy, benzoyl, $C_1$-$C_4$ haloalkyl, $C_2$-$C_5$ alkoxycarbonyl, CN or $NO_2$ substituent; tetrahydropyranyl; tetrahydropyranyl having a $C_1$-$C_4$ alkoxy or halogen substituent; tri-($C_1$-$C_4$ alkyl)silyl; $C_1$-$C_6$ alkyl; mono- or di-$C_1$-$C_4$ alkoxymethyl; mono- or di- $C_1$-$C_4$ alkoxymethyl having a $C_1$-$C_4$ alkoxy or halogen substituent; benzyl; benzyl having a $C_1$-$C_4$ alkyl, $C_1$-$C_4$ alkoxy, halogen, $NO_2$ or CN substituent; $C_2$-$C_7$ alkoxycarbonyl, $C_2$-$C_7$ alkoxycarbonyl having a halogen or tri-($C_1$-$C_4$ alkyl)silyl substituent; benzyloxycarbonyl; benzyloxycarbonyl having a $C_1$-$C_4$ alkoxy or $NO_2$ substituent; and $C_2$-$C_6$ aliphatic acyloxy-, benzoyloxy- or substituted benzoyloxy-methoxycarbonyl;

$R^2$ represents a hydrogen atom, a hydroxy group or a protected hydroxy group selected from the hydroxy-protecting group specified for $R^1$;

$R^3$ and $R^4$ are independently selected from the group consisting of hydrogen atoms and carboxy-protecting groups selected from the group consisting of $C_1$-$C_6$ alkyl; $C_1$-$C_6$ haloalkyl; mono-, di- or tri-$C_6$-$C_{14}$ arylmethyl; mono-, di- or tri- $C_6$-$C_{14}$ arylmethyl having aryl moiety substituted with a $C_1$-$C_4$ alkoxy, $C_1$-$C_4$ alkyl, halogen or $C_{1-2}$ alkylenedioxy substituent; $C_2$-$C_6$ aliphatic acyloxymethyl; $C_1$-$C_6$ alkoxymethyl; $C_1$-$C_6$ alkoxymethyl having a $C_1$-$C_4$ alkoxy substituent; 1-($C_1$-$C_6$ alkoxy)carbonyloxyethyl; phthalidyl; and (2-oxo-5-methyl-1,3-dioxolen-4-yl)methyl;

$R^5$ and $R^6$ each represent hydrogen atom or together represent an extra carbon-carbon bond between the carbon atoms to which they are attached; and $R^7$ represents an alkyl group or an aralkyl group;

which process comprises reacting a compound of formula (II):

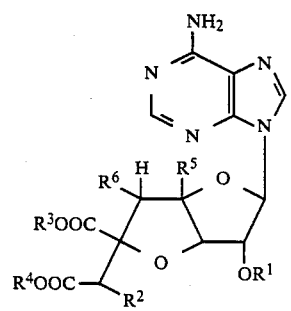

with a compound of formula (III):

$$R^7-X \quad (III)$$

to bond said $R^7$ group to the No. 1 ring nitrogen atom of the compound and contacting said compound having the $R^7$ group bonded to the No. 1 nitrogen atom with a liquid having a pH of at least 4 whereby the aminopyrimidine ring containing said No. 1 nitrogen atom is cleaved, rearranged and reformed thereby removing the $R^7$ group from the No. 1 ring nitrogen atom and bonding it to the $N^6$ nitrogen atom.

2. The process as claimed in claim 1, wherein said compound of the formula (I) is salified.

3. The process as claimed in claim 1, wherein a compound of formula (II) is reacted with a compound of formula (III) in said liquid having a pH of at least 4.

4. The process as claimed in claim 1, wherein a compound of the formula (II) is reacted with the compound of the formula (III) to bond said $R^7$ group to the No. 1 ring nitrogen atom of the compound, and then said compound having the $R^7$ group bonded to the No. 1 nitrogen atom is contacted with said liquid having a pH of at least 4.

5. The process as claimed in claim 1, wherein at least one of said $R^1$, $R^2$, $R^3$ and $R^4$ is one of said protected groups, and wherein said at least one protected group is removed to form the compound of the formula (I).

6. The process as claimed in claim 1, wherein said pH is from 4 to 12.

7. The process as claimed in claim 1, wherein said pH is at least 7.

8. The process as claimed in claim 3, wherein said cleaving, rearrangement and ring-closure reactions are effected in a medium of pH at least 10.

9. The process as claimed in claim 1, wherein said cleaving, rearrangement and ring-closure reactions are effected at ambient temperature.

10. The process as claimed in claim 1, wherein the reaction of said compounds of formulae (II) and (III) is effected at a temperature of from 0° to 100° C.

11. The process as claimed in claim 1, wherein X represents a halogen atom.

12. The process as claimed in claim 1, wherein $R^7$ represents a methyl group.

13. The process as claimed in claim 12, wherein said cleaving, rearrangement and ring-closure reactions are effected by heating at a pH of at least 4.

14. The process as claimed in claim 13, wherein said pH is from 4 to 12.

15. The process as claimed in claim 13, wherein said pH is at least 7.

16. The process as claimed in claim 1, wherein said cleaving, rearrangement and ring-closure reactions are effected in a medium of pH at least 10 and heating.

17. The process as claimed in claim 12, wherein said ring-opening, rearrangement and ring-closure reactions are effected at ambient temperature.

18. A process for preparing compounds of formula (I):

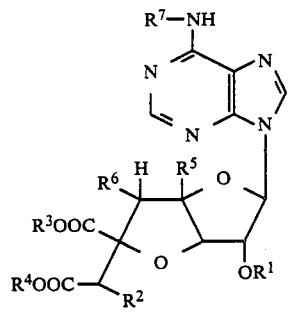

wherein:
$R^1$ represents a hydrogen atom or a hydroxy-protecting group;
$R^2$ represents a hydrogen atom, a hydroxy group or a protected hydroxy group;
$R^3$ and $R^4$ are independently selected from the group consisting of hydrogen atoms and carboxy-protecting groups;
$R^5$ and $R^6$ each represent hydrogen atoms or together represent an extra carbon-carbon bond between the carbon atoms to which they are attached; and
$R^7$ represents an alkyl group or an aralkyl group;
which process comprises the steps:
(a) reacting a compound of formula (II):

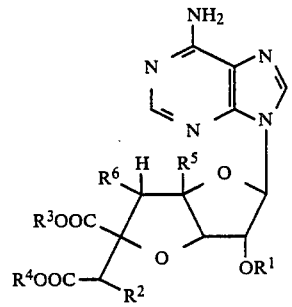

with a compound of formula (III):

$$R^7-X \quad (III)$$

wherein X represents a halogen atom, a $C_1$-$C_6$ alkylsulfonyloxy group, a fluorinated $C_1$-$C_6$ alkylsulfonyloxy group, an arylsulfonyloxy group or a $C_1$-$C_6$ alkoxysulfonyloxy group;
to bond said $R^7$ group to the No. 1 ring nitrogen atom of the compound, and then
(b) contacting said compound having the $R^7$ group bonded to the No. 1 nitrogen atom with a liquid having a pH of from 4 to 12 and at a temperature of from 0 to 100° C. whereby the aminopyrimidine ring containing said No. 1 nitrogen atom is cleaved, rearranged and reformed thereby removing the $R^7$ group from the No. 1 ring nitrogen atom and bonding it to the $N^6$ nitrogen atom.

19. The process as claimed in claim 18, wherein said cleaving, rearrangement and ring-closure reactions in step (b) are effected by heating said product at said pH from 4 to 12.

20. The process as claimed in claim 19, wherein said pH is at least 7.

21. The process as claimed in claim 18, wherein said cleaving, rearrangement and ring-closure reactions in step (b) are effected in a medium of pH at least 10.

22. The process as claimed in claim 21, wherein said cleaving, rearrangement and ring-closure reactions are effected at ambient temperature.

23. The process as claimed in claim 18, wherein X represents a halogen atom.

24. The process as claimed in claim 18, wherein $R^7$ represents a methyl group.

25. The process as claimed in claim 18, wherein said compound of the formula (I) is salified.

26. The process as claimed in claim 18, wherein at least one of said $R^1$, $R^2$, $R^3$ and $R^4$ is one of said protected groups, and wherein said at least one protected group is removed to form the compound of the formula (I).

* * * * *